United States Patent [19]

Butler et al.

[11] 4,386,094

[45] May 31, 1983

[54] 4-LOWER ALKYL-3-PHENOXYPYRIDINE-1-OXIDE AND A METHOD FOR ITS PRODUCTION

[75] Inventors: Donald E. Butler, Ann Arbor; Ivan C. Nordin, Holland, both of Mich.

[73] Assignee: Warner-Lambert Company, Morris Plains, N.J.

[21] Appl. No.: 179,365

[22] Filed: Aug. 18, 1980

[51] Int. Cl.$^3$ ................... C07D 213/89; A61K 31/44
[52] U.S. Cl. ..................................... 424/263; 546/290
[58] Field of Search ........................ 546/290; 424/263

[56] References Cited

U.S. PATENT DOCUMENTS

| | | | |
|---|---|---|---|
| 3,721,676 | 3/1973 | Witzel et al. | 546/290 |
| 4,187,311 | 2/1980 | Butler | 424/263 |
| 4,187,379 | 2/1980 | Butler | 424/263 |

FOREIGN PATENT DOCUMENTS

| | | | |
|---|---|---|---|
| 2714041 | 10/1977 | Fed. Rep. of Germany | 546/290 |
| 838746 | 6/1960 | United Kingdom | 546/290 |

OTHER PUBLICATIONS

Villani et al., Jour. of Medicinal Chemistry, vol. 18, No. 1, (1975), pp. 1–8.

*Primary Examiner*—John M. Ford
*Attorney, Agent, or Firm*—Ronald A. Daignault

[57] ABSTRACT

4-Lower alkyl-3-phenoxypyridine-1-oxides, pharmacological agents possessing anticonvulsant properties, pharmaceutical compositions and methods of using said compositions are disclosed. These compounds are produced by reacting 4-lower alkyl-3-phenoxypyridines with an oxidizing agent.

9 Claims, No Drawings

4-LOWER ALKYL-3-PHENOXYPYRIDINE-1-OXIDE AND A METHOD FOR ITS PRODUCTION

SUMMARY AND DETAILED DESCRIPTION

The present invention relates to 4-lower alkyl-3-phenoxypyridine-1-oxides, pharmaceutical compositions containing said compounds and methods of using said compounds and compositions in the treatment of mammals which may be subject to convulsions, namely epileptic seizures and to methods for the preparation of said compounds and pharmaceutical compositions.

In accordance with the invention 4-lower alkyl-3-phenoxypyridine-1-oxides having the formula

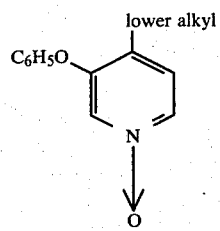

can be produced by reacting 4-lower alkyl-3-phenoxypyridines with an oxidizing agent of the type generally employed to covert amines to N-oxides, such as 3–30 percent hydrogen peroxide in water, 5–40 percent peracetic acid in acetic acid, perbenzoic acid, pertrifluoroacetic acid, perphthalic acid, m-chloroperbenzoic acid, etc. with the preferred being 40 percent peracetic acid. Although equimolar amounts of the two reactants may be employed, preferably an excess of oxidizing agent is used. While the amount in excess is not critical, one may use as much as a two fold excess or even more. The solvent system may be any generally used in oxidation reactions of this type with the preferred being glacial acetic acid, mixtures of water in acetic acid, halogenated hydrocarbons, such as dichloromethane, chloroform, or tetrachloroethane. The most preferred is glacial acetic acid. The reaction is carried out at temperatures of from about 0° C. to about 100° C. for from one to twenty-four hours, preferably 55° C. to 60° C. for approximately sixteen hours. The product is isolated by distillation.

The term "lower alkyl" is intended to mean a hydrocarbon moiety having from one to four carbon atoms; such as methyl, ethyl, propyl, iso-propyl, butyl, n-butyl, s-butyl, butyl, t-butyl, cyclopropyl, cyclobutyl, propenyl, allyl, 1-butenyl, etc. The preferred compound is that wherein "lower alkyl" is methyl.

The described compounds of the invention are intended to include solvates such as the hydrate and stereoisomers or regioisomers and mixtures thereof depending upon the structure of the lower alkyl group.

4-Lower alkyl-3-phenoxypyridine-1-oxides are administered for the purpose of treating convulsions or preventing the onset of convulsions in mammals, such as rodents, dogs, cats, etc. The specific profile of this compound indicates its use would be in treating conditions where antiepileptic agents such as phenytoin and carbamazepine and to a lesser extent mephenyltoin are traditionally employed.

The utility of the aforementioned compound as an anticonvulsant is determined by generating a compound profile using three tests. The tests employed are described in Epilepsia 19 (1978) 409–428 which is incorporated by reference.

The tests were performed by the National Institute of Neurological and Communicative Disorders and Stroke and used male Carworth Farms No. 1 mice. The compounds are employed at at least 3 dose levels (30, 100, 300 mg/kg) in the following three tests.

MES—Maximal Electroshock Seizure Test

Maximal electroshock seizures are elicited with a 60 cycle alternating current of 50 mA intensity (5–7 times that necessary to elicit minimal electroshock seizures) delivered for 0.2 sec via corneal electrodes. A drop of 0.9% saline is instilled in the eye prior to application of the electrodes in order to prevent the death of the animal. Abolition of the hind limb tonic extension component of the seizure is defined as protection and results are expressed as:

number of animals protected/number of animals tested.

sc Met—Subcutaneous Pentylenetetrazol (Metrazol®) Seizure Threshold Test 85 mg/kg of pentylenetetrazol (produces seizures in greater than 95% of mice) is administered as a 0.5% solution subcutaneously in the posterior midline. The animal is observed for 30 minutes. Failure to observe even a threshold seizure (a single episode of clonic spasms of at least 5 sec duration) is defined as protection and the results are expressed as:

number of animals protected/number of animals tested.

Tox—Toxicity

The Rotorod test is used to evaluate neurotoxicity. The animal is placed on a 1 inch diameter knurled plastic rod rotating at 6 rpm. Normal mice can remain on a rod rotating at this speed indefinitely. Neurologic toxicity is defined as the failure of the animal to remain on the rod for 1 minute, and is expressed as:

number of animals exhibiting toxicity/number of animals tested.

| | | | ROTOROD TD50 (mg/kg) | | MES-ED50 (mg/kg) | | sc Met-ED50 (mg/kg) | |
|---|---|---|---|---|---|---|---|---|
| | TIME OF TEST (hrs) | | | | | | | |
| SUBSTANCE | MICE | RATS | MICE | RATS | MICE | RATS | MICE | RATS |
| | | | | | [3.47] | [6.80] | | |
| 4-METHYL-3-PHENOXY-PYRIDINE-1-OXIDE | ½, | ½,— | 296.18 (250.60–344.01) [8.32] | 76.07 (58.13–94.79) [5.16] | 85.29 (68.68–102.95) [5.26] | 11.19 (8.77–13.80) [5.89] | Potentiates | Potentiates |

PROFILE OF ANTICONVULSANT ACTIVITY ON ORALLY ADMINISTERED 4-METHYL-3-PHENOXYPYRIDINE-1-OXIDE SOME PROTOTYPE ANTIEPILEPTICS IN MICE

PROFILE OF ANTICONVULSANT ACTIVITY ON ORALLY ADMINISTERED 4-METHYL-3-PHENOXYPYRIDINE-1-OXIDE SOME PROTOTYPE ANTIEPILEPTICS IN MICE
-continued

| SUBSTANCE | TIME OF TEST (hrs) MICE | RATS | ROTOROD TD50 (mg/kg) MICE | RATS | MES-ED50 (mg/kg) MICE | RATS | sc Met-ED50 (mg/kg) MICE | RATS |
|---|---|---|---|---|---|---|---|---|
| PHENY-TOIN | 2,2,— | ½,4 | 86.71 (80.39–96.09) [13.01] | >3000 | [9.59] 9.04 (7.39–10.62) [6.28] | [>100] 29.82 (21.92–38.91) [2.82] | Ineffective | Ineffective |
| MEPHENY-TOIN | 1½, 1½ | 2,2 | 97.0* (85.0–110.6) | 143* (106–193) | [2.62] 37.0 (24.8–55.1) | [14.30] 10 (8.7–11.6) | [1.83] 53.0 (35.8–78.5) | [1.30] 105 (72–154) |
| CARBAMA-ZEPINE | ½, ½ | 2,1 | 217.21 (131.49–270.11) [3.47] | 813.06 (488.76–1233.87) [6.07] | [14.06] 15.44 (12.44–17.31) [9.07] | [95.65] 8.50 (3.39–10.53) [4.50] | [4.52] 48.07 (40.75–57.35) [5.50] | Variable |

*Data from Swinyard, Brown, and Goodman, J. Pharmacol. & Exper. Therap. 106, 319–330, 1952.
**Data from Swinyard, Orr, Jolley, and Goodman. Fed. Proc. 9, 319, 1950
[ ] Slope, regression line
( ) 95% Confidence intervals
Data in small square is a protective index. The protective index is the rotorod toxicity dose divided by the minimal effective anticonvulsant dose.

PROFILE OF ANTICONVULSANT ACTIVITY OF INTRAPERITONEALLY ADMINISTERED 4-METHYL-3-PHENOXYPYRIDINE-1-OXIDE SOME PROTOTYPE ANTIEPILEPTICS IN MICE

| SUBSTANCE | TIME OF TEST (hrs) | TD50 (mg/kg) | ED50 (mg/kg) and PI | | | | |
|---|---|---|---|---|---|---|---|
| | | | MES | sc Met | Bicuculline | Picrotoxin | Strychnine |
| 4-METHYL-3-PHENOXY-PYRIDINE-1-OXIDE | ½, ½ | 76.25 (71.34–80.89) [24.50] | [3.28] 23.22 (20.53–26.61) [11.23] | Potentiates | Potentiates | Potentiates | Ineffective |
| PHENY-TOIN | 2,2 | 65.46 (52.49–72.11) [15.23] | [6.89] 9.50 (8.13–10.44) [13.66] | Potentiates | Potentiates | Potentiates | Max. Prot. 50% at 55–100 mg/kg |
| MEPHENY-TOIN | ½, ½ | 153.82 (132.86–178.73) [9.22] | [2.54] 60.50 (49.45–70.25) [8.01] | [5.05] 30.45 (19.67–39.47) [4.76] | [1.24] 124.14 (84.10–188.49) [1.99] | [1.52] 100.96 (79.34–122.92) [7.43] | Max. Prot. 50% at 70–150 mg/kg |
| CARBAM-AZEPINE | ½, ½ | 71.56 (45.91–134.79) [4.77] | [8.12] 8.81 (5.45–14.09) [3.62] | Potentiates | Max. Prot. 62.5% at 50–130 mg/kg. | [1.92] 37.20 (25.32–59.69) [3.86] | [0.91] 78.83 (39.39–132.03) [2.85] |

( ) Confidence Levels; 95%
[ ] Slope, regression line
Data in small square is a Protective Index. The Protective Index is the rotorod toxicity dose divided by the minimal effective anticonvulsant dose.

4-Lower alkyl-3-phenoxypyridine-1-oxides are useful anticonvulsants in mammals such as dogs, cats, horses, sheep, etc., when administered in amounts ranging from about 0.014 mg to about 21.4 mg per kg. of body weight per day. A preferred dosage regimen for optimum results would be from about 0.36 mg to about 10.7 mg per kg of body weight per day, and such dosage units are employed that a total of from about 1 mg to about 1500 mg of active ingredient for a subject of about 70 kg body weight are administered in a 24 hour period, preferably 25 mg to 750 mg/day.

The compounds of the present invention in the described dosages are intended to be administered orally; however, other routes such as rectally, intraperitoneally, subcutaneously, intramuscularly or intravenously may be employed. Of the routes other than oral, the most important is the intravenous route.

The active compounds of the present invention may be orally administered, for example, with an inert diluent or with an assimilable edible carrier, or they may be enclosed in hard or soft gelatin capsules. In addition, they may be compressed into tablets, or may be incorporated directly with the food of the diet. For oral therapeutic administration, the active compounds of this invention may be incorporated with excipients and used in the form of tablets, troches, or capsules. Other less frequently used solid formulations include wafers, chewing gum, and the like. Liquid formulations may include solutions or suspension (elixirs, syrups, etc.) Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between 1.0 and 50 milligrams of active compound.

The tablets, troches, pills, capsules and the like may also contain the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier, such as a fatty oil or a solid carrier, such as lactose. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

When used in the form of a suppository, the compound of the invention should be dispersed in a carrier, such as glycerine, cocoa butter, etc.

Parenteral preparations such as those of the intravenous, intramuscular, etc. type, may be in the form of sterilized aqueous solutions containing buffering agents, preservatives, salts to control isotonicity, etc. or lyphilized materials which may be either the pure sterilized compound or a mixture containing additives, such as buffering agents (phosphate buffers), salts (sodium chloride), preservatives (benzalkonium chloride), etc. The pure sterile compound can be dissolved in standard injectable solutions, such as Ringer's Solution, while the mixtures would be dissolved in water for injection.

The invention will be described in greater detail in conjunction with the following specific examples.

EXAMPLE 1

A solution of 25 g of 4-methyl-3-phenoxypyridine, [J.Med.Chem., 18, 1 (1975)] in 90 ml of glacial acetic acid is treated with 30 ml of 40% peracetic acid in acetic acid and the mixture is stirred and heated at 60° C. for 12 hours. Two further 10 ml portions of 40% peracetic acid are added and the mixture heated 4 hours at 60° C. 100 ml of isopropanol is added and the mixture is heated at 90° C. for 4 hours. The mixture is stripped at reduced pressure and dissolved in 500 ml of dichloromethane. The organic layer is washed with an excess of 25% sodium hydroxide solution, dried over anhydrous magnesium sulfate, filtered, concentrated, and distilled to yield 4-methyl-3-phenoxypyridine-1-oxide. B.P. 150°–152° C./0.3 mm

EXAMPLE 2

| Ingredient | Quantity |
| --- | --- |
| 4-Methyl-3-phenoxypyridine-1-oxide | 150 g |
| Lactose | 1124 g |
| Corn Starch | 39 g |
| Hydroxypropyl Cellulose | 30 g |
| Magnesium Stearate | 7 g |
| Ethanol-water 50:50 | qs |

The 4-methyl-3-phenoxypyridine-1-oxide, lactose, and hydroxypropyl cellulose are blended and granulated with 50:50 ethanol-water. The wet granulation is screened, dried, and rescreened. The resulting dried granulation is blended with magnesium stearate and the corn starch, and the mixture is compressed into 225 mg tablets using 11/32 inch standard concave punches. Yield equals approximately 6000 tablets each containing 25 mg of 4-methyl-3-phenoxypyridine-1-oxide.

EXAMPLE 3

| Ingredient | Quantity |
| --- | --- |
| 4-Methyl-3-phenoxypyridine-1-oxide | 15 g |
| Lactose | 1249 g |
| Corn Starch | 39 g |
| Hydroxypropyl Cellulose | 30 g |
| Magnesium Stearate | 7 g |
| Ethanol-water 50:50 | qs |

The 4-methyl-3-phenoxypyridine-1-oxide, lactose, and hydroxypropyl cellulose are blended and granulated with 50:50 ethanol-water. The wet granulation is screened, dried, and rescreened. The resulting dried granulation is blended with magnesium stearate and the corn starch, and the mixture is compressed into 225 mg tablets using 11/32 inch standard concave punches. Yield equals approximately 6000 tablets each containing 2.5 mg of 4-methyl-3-phenoxypyridine-1-oxide.

EXAMPLE 4

| Ingredient | Quantity |
| --- | --- |
| 4-Methyl-3-phenoxypyridine-1-oxide | 6 g |
| Lactose | 1268 g |
| Corn Starch | 39 g |
| Hydroxypropyl Cellulose | 30 g |
| Magnesium Stearate | 7 g |
| Ethanol-water 50:50 | qs |

The 4-methyl-3-phenoxypyridine-1-oxide, lactose, and hydroxypropyl cellulose are blended and granulated with 50:50 ethanol-water. The wet granulation is screened, dried, and rescreened. The resulting dried granulation is blended with magnesium stearate and the corn starch, and the mixture is compressed into 225 mg tablets using 11/32 inch standard concave punches. Yield equals approximately 6000 tablets each containing 1.0 mg of 4-methyl-3-phenoxypyridine-1-oxide.

EXAMPLE 5

| Ingredient | Quantity |
| --- | --- |
| 4-Methyl-3-phenoxypyridine-1-oxide | 300 g |
| Lactose | 974 g |
| Corn Starch | 39 g |
| Hydroxypropyl Cellulose | 30 g |

-continued

| Ingredient | Quantity |
| --- | --- |
| Magnesium Stearate | 7 g |
| Ethanol-water 50:50 | qs |

The 4-methyl-3-phenoxypyridine-1-oxide, lactose, and hydroxypropyl cellulose are blended and granulated with 50:50 ethanol-water. The wet granulation is screened, dried, and rescreened. The resulting dried granulation is blended with magnesium stearate and the corn starch, and the mixture is compressed into 225 mg tablets using 11/12 inch standard concave punches. Yield equals approximately 6000 tablets each containing 50 mg of 4-methyl-3-phenoxypyridine-1-oxide.

EXAMPLE 6

| Ingredient | Quantity |
| --- | --- |
| 4-Methyl-3-phenoxypyridine-1-oxide | 250 g |
| Lactose | 1723 g |
| Magnesium Stearate | 27 g |

The mixture is blended and filled into No. 4 hard gelatin capsules, filling each capsule with 200 mg of the powder mixture. Yield equals approximately 10,000 capsules each containing 25 mg of 4-methyl-3-phenoxypyridine-1-oxide.

EXAMPLE 7

| Ingredient | Quantity |
| --- | --- |
| 4-Methyl-3-phenoxypyridine-1-oxide | 25 g |
| Lactose | 1948 g |
| Magnesium Stearate | 27 g |

The mixture is blended and filled into No. 4 hard gelatin capsules, filling each capsule with 200 mg of the powder mixture. Yield equals approximately 10,000 capsules each containing 2.5 mg of 4-methyl-3-phenoxypyridine-1-oxide.

EXAMPLE 8

| Ingredient | Quantity |
| --- | --- |
| 4-Methyl-3-phenoxypyridine-1-oxide | 250 g |
| Lactose | 1963 g |
| Magnesium Stearate | 27 g |

The mixture is blended and filled into No. 4 hard gelatin capsules, filling each capsule with 200 mg of the powder mixture. Yield equals approximately 10,000 capsules each containing 1. mg of 4-methyl-3-phenoxypyridine-1-oxide.

EXAMPLE 9

| Ingredient | Quantity |
| --- | --- |
| 4-Methyl-3-phenoxypyridine-1-oxide | 500 g |
| Lactose | 1473 g |
| Magnesium Stearate | 27 g |

The mixture is blended and filled into No. 4 hard gelatin capsules, filling each capsule with 200 mg of the powder mixture. Yield equals approximately 10,000 capsules each containing 50 mg of 4-methyl-3-phenoxypyridine-1-oxide.

EXAMPLE 10

| Ingredient | Quantity |
| --- | --- |
| 4-Methyl-3-phenoxypyridine-1-oxide | 1.0 g |
| Phemerol Chloride Recrystallized | 0.1 g |
| Water for Injection USP | qs ad 1.0 ml |

The 4-methyl-3-phenoxypyridine-1-oxide is mixed with about two-thirds of the required volume of Water for Injection USP followed by the addition of sufficient Water for Injection to reach the desired volume. After mixing, the solution is sterilized by membrane filtration (a 0.22 micron Millipore filter membrane represents a suitable filter). The desired quantity of the above prepared solution is filled into appropriate size multiple dose vials suitable for injection preparations and stoppered with gum rubber or suitable rubber closures and sealed with aluminum ferrules. The preparation may also be filled into suitable size single dose glass ampoules and sealed.

Using the above procedure, solutions containing 1.0, 2.5, 5.0, or 10.0 mg/ml of 4-methyl-3-phenoxypyridine-1-oxide may be prepared.

We claim:
1. 4-Loweralkyl-3-phenoxypyridine-1-oxide.
2. The compound of claim 1 having the name, 4-methyl-3-phenoxypyridine-1-oxide.
3. A pharmaceutical composition useful for treating convulsions in a mammal which comprises an anticonvulsive effective amount of a 4-loweralkyl-3-phenoxypyridine-1-oxide in combination with a pharmaceutically acceptable carrier.
4. The composition defined in claim 3 which comprises the compound, 4-methyl-3-phenoxypyridine-1-oxide.
5. The composition defined in claim 3 which comprises from about 0.5 mg to about 100 mg of a 4-loweralkyl-3-phenoxypyridine-1-oxide.
6. The composition defined in claim 3 which comprises from about 1.0 mg to about 50 mg of 4-methyl-3-phenoxypyridine-1-oxide.
7. A method for treating mammals having epilepsy which comprises administering an antiepileptically effective amount of a composition defined in claim 3.
8. The method defined in claim 7 wherein about 0.014 mg/kg to about 21.4 mg/kg of weight of a 4-loweralkyl-3-phenoxypyridine-1-oxide is administered per day.
9. The method defined in claim 7 wherein 0.36 mg/kg to 10.7 mg/kg of weight of 4-methyl-3-phenoxypyridine-1-oxide is administered per day.

* * * * *